United States Patent
Bluecher et al.

(10) Patent No.: US 10,758,380 B2
(45) Date of Patent: Sep. 1, 2020

(54) STENTS WITH IMPROVED FIXATION

(71) Applicant: BVW Holding AG, Cham (CH)

(72) Inventors: Lukas Bluecher, Eurasberg (DE); Michael Milbocker, Holliston, MA (US); Roel Trip, Atlanta, GA (US)

(73) Assignee: BVW Holding AG, Cham (CH)

(*) Notice: Subject to any disclaimer, the term of this patent is extended or adjusted under 35 U.S.C. 154(b) by 152 days.

(21) Appl. No.: 15/859,440

(22) Filed: Dec. 30, 2017

(65) Prior Publication Data
US 2018/0193175 A1    Jul. 12, 2018

Related U.S. Application Data

(60) Provisional application No. 62/441,087, filed on Dec. 30, 2016.

(51) Int. Cl.
*A61F 2/88* (2006.01)
*A61F 2/07* (2013.01)
(Continued)

(52) U.S. Cl.
CPC ............ *A61F 2/88* (2013.01); *A61F 2/07* (2013.01); *A61F 2/90* (2013.01);
(Continued)

(58) Field of Classification Search
CPC ...... A61F 2/88; A61F 2/07; A61F 2/90; A61F 2002/044; A61F 2002/045;
(Continued)

(56) References Cited

U.S. PATENT DOCUMENTS

| 5,876,448 A | 3/1999 | Thompson et al. |
| 6,585,747 B1 | 7/2003 | Limon et al. |

(Continued)

FOREIGN PATENT DOCUMENTS

| WO | 2009158336 A1 | 12/2009 |
| WO | 2010096073 A1 | 8/2010 |

OTHER PUBLICATIONS

PCT Search and Written Opinion for corresponding PCT Application No. PCT/US2017/069150, filed Dec. 30, 2017, dated Apr. 3, 2018, 14 pages.

*Primary Examiner* — Christopher D. Prone
*Assistant Examiner* — Tiffany P Shipmon
(74) *Attorney, Agent, or Firm* — Patterson Intellectual Property Law, P.C.; Ryan D. Levy; Mark A. Kilgore (57) ABSTRACT

The present disclosure provides stents, particularly self-expanding stents, useful for the GI tract, and more particularly, useful for treating esophageal strictures. The stents provided herein include a medial region and proximal and distal cuffs having external diameters greater than the medial region diameter when the stent is in the deployed state. The medial region comprises an open weave wire construction. An elastomeric coating circumscribes the medial region, while the may be an extension of the wire construction or separate elements. Preferably, the cuffs have a textured surface for contact with the esophageal wall tissue to resist stent migration. The elastomer coated medial region provides a barrier to tissue ingrowth, and has an enhanced radial restoring force to maintain an open passageway in a body lumen. Optionally, the stent includes an exterior sheath with a surface pattern, to which the stent couples. A low durometer sleeve, between the stent and body lumen, axial positioning of the stent relative to the body lumen. Consequently, precision in stent placement is provided without tissue damage that could result if positioning motion occurred between the surface texture and the body lumen.

14 Claims, 8 Drawing Sheets

(51) Int. Cl.
*A61F 2/90* (2013.01)
*A61F 2/04* (2013.01)

(52) U.S. Cl.
CPC ... *A61F 2002/044* (2013.01); *A61F 2002/045* (2013.01); *A61F 2002/072* (2013.01); *A61F 2002/075* (2013.01); *A61F 2210/0004* (2013.01); *A61F 2230/0065* (2013.01); *A61F 2250/0003* (2013.01); *A61F 2250/0025* (2013.01); *A61F 2250/0026* (2013.01); *A61F 2250/0039* (2013.01); *A61F 2250/0048* (2013.01); *A61F 2250/0051* (2013.01); *A61F 2250/0056* (2013.01); *A61F 2250/0067* (2013.01)

(58) Field of Classification Search
CPC .......... A61F 2002/072; A61F 2002/075; A61F 2210/0004; A61F 2230/0065; A61F 2250/0003; A61F 2250/0025; A61F 2250/0026; A61F 2250/0039; A61F 2250/0048; A61F 2250/0051; A61F 2250/0056; A61F 2250/0067
See application file for complete search history.

(56) References Cited

U.S. PATENT DOCUMENTS

| | | |
|---|---|---|
| 7,588,596 B2 | 9/2009 | Spiridigliozzi et al. |
| 7,993,410 B2 | 8/2011 | Shin et al. |
| 8,057,461 B2 | 11/2011 | Deal |
| 8,092,482 B2 | 1/2012 | Gannoe et al. |
| 8,435,283 B2 | 5/2013 | Jordan et al. |
| 8,556,962 B2 | 10/2013 | Bates et al. |
| 8,597,366 B2 | 12/2013 | Shank |
| 8,758,428 B2 | 6/2014 | Bates et al. |
| 8,834,558 B2 | 9/2014 | Nissl |
| 9,265,635 B2 | 2/2016 | Walak |
| 9,327,058 B2 | 5/2016 | Isch |
| 9,439,790 B2 | 9/2016 | Clerc et al. |
| 9,469,925 B2 | 10/2016 | Mcmahon et al. |
| 9,498,319 B2 | 11/2016 | Walak |
| 9,517,122 B2 | 12/2016 | Firstenberg et al. |
| 9,526,640 B2 | 12/2016 | Bertolino et al. |
| 2013/0268044 A1* | 10/2013 | Parsons ............ A61F 2/07 623/1.2 |
| 2014/0277395 A1* | 9/2014 | Firstenberg ........ A61F 2/07 623/1.36 |
| 2015/0282955 A1 | 10/2015 | Guler et al. |

* cited by examiner

STENTS WITH IMPROVED FIXATION

CROSS-REFERENCE TO RELATED APPLICATIONS

This application claims benefit of U.S. Provisional Application No. 62/441,087 filed on Dec. 30, 2016, which is hereby incorporated by reference in its entirety.

TECHNICAL FIELD

The present disclosure provides stents, particularly esophageal stents, comprising a micro-textured surface, and a method of manufacturing thereof. The micro-textured surface advantageously contacts esophageal surfaces and reduces or prevents stent migration.

BACKGROUND OF THE INVENTION

The present disclosure relates to implantable treatment devices, and more particularly to stents and other prostheses intended for fixation in body lumens especially including the esophagus Stents are generally employed to open or keep open a body lumen. For example, carcinomas in the esophagus lead to progressive dysphagia, i.e. difficulty in swallowing, and the inability to swallow liquids in the most severe cases. While surgical removal is sometimes effective, the majority of patients have tumors that cannot be surgically removed. Repeated dilations of the body lumen of the esophagus provide only temporary relief.

Difficult or refractory cases often are treated by intubation using open wire weave prostheses or stents. An example of an open wire weave stent is provided in U.S. Pat. No. 4,800,882 (Gianturco), wherein is described such a device employed as an endovascular stent. These prostheses are frequently subject to migration. Self-expanding mesh stents also have been considered for use as esophageal prostheses. U.S. Pat. No. 4,655,771 (Wallsten) discloses a mesh stent as a flexible tubular braided structure formed of helically wound thread elements. Mesh stents appear unlikely to lead to pressure necrosis of the esophageal wall. The inherent scalability of mesh stents, as compared to a rigid plastic stents, makes them more easily inserted and the subsequent implantation causes much less trauma to the patient.

A difficulty with self-expanding stents concerns their accurate placement and deployment. Typically a tube surrounds the self-expanding stent and radially compresses the stent into a reduced-radius delivery configuration. With the stent positioned at a treatment site, the outer tube is axially withdrawn, permitting the stent to radially self-expand. However, the larger size of an esophageal stent (as compared to biliary and vascular applications, for example) gives rise to substantial friction at the stent/outer tubing interface. As a result, it is difficult to precisely maintain the position of the stent during deployment, and practically impossible to retract the stent after partial deployment.

Migration resistant stent designs include the addition of a mechanically lumen-bonding surface to the outer surface of a stent. U.S. Pat. No. 8,435,283 (Jordan et al) describes the addition of a cross hatch pattern of pyramids to the outer surface of a stent. The texture is intended to mechanically grasp tissue, and thereby anchor the stent. Such stents suffer from the disadvantage that dislocation by peristaltic motion causes inflammation of the inner lining of the body lumen, leading to infection, necrosis and possibly perforation.

Stenting of the esophagus has proven to be a particularly challenging stent application. The esophagus is a muscular lumen that is about ten inches long and extends from the hypopharynx to the stomach. The esophageal lumen is subject to wavelike contractions known as peristalsis, which pushes food down through the esophagus to the stomach.

Conventional stents utilized for the esophagus have significant drawbacks. Because the esophagus is very soft and flexible compared to other lumina, preventing migration of the stent is problematic. In particular, the esophagus frequently changes size and position, which causes complications for typical stents. For instance, a stent having a constant diameter along its entire axial length will have a tendency to migrate as the esophagus expands. The stricture is narrower than the lumen located proximally and distally of the stricture, and the stent is longer than the length of the stricture such that the portions of the stent proximately and distally of the stricture do not help prevent the stent from migrating. Therefore, there is an increased possibility that the stent will migrate within the lumen.

Moreover, the esophageal lumen is muscular and its wavelike contractions generally travel from its proximal end to its distal end resulting from an impulse applied at one side of the lumen wall. Due to the actions of the lumen, flexible stents have been designed to mimic the movement of the lumen. However, flexible stents may be prone to infolding or kinking, effectively occluding one or both of the openings of the stent. Furthermore, providing more rigid stents increases the risk of damage to the lumen of the esophagus, such as by damaging the blood vessels lining the lumen. Rigid stents are also typically more prone to migration.

A further difficulty with self-expanding esophageal stents is that they can cause gastrointestinal reflux. To place the self-expandable esophageal stent at a lesioned part of the stenosed gullet, an operator primarily shrinks the stent so as to reduce the cross section of the stent, installs the shrunken stent in a stent insertion device, and inserts the stent into the stenosed part of the gullet using the insertion device. After the stent reaches the stenosed part of the gullet, the stent is pushed so that the stent, usually fabricated from shape-memory alloy wires, is separated from the insertion device and elastically expands and restores its original shape, thus pushing the wall of the stenosed part outwards in radial directions and thereby enlarging the size of the passage of the stenosed part, making swallowing easier.

However, when the esophagus is stenosed near the stomach, where the esophageal sphincter is located, the esophageal stent must be placed in the lower end of the esophagus. Low end esophageal placement can open the esophageal sphincter causing gastrointestinal reflux. The presence of stomach acid in the esophagus can significantly complicate an already pathologic condition.

Accordingly, there is a need in the industry for a stent that is capable of conforming to a lumen and maintaining the opening through a stricture. In addition, there is a need for a stent that reduces migration and the possibility of obstruction of the stent openings.

BRIEF SUMMARY OF THE INVENTION

With these considerations in mind, the present disclosure provides a stent device possessing an exterior (body lumen contacting) textured surface to prevent stent migration. A further object of the disclosure is to provide a radially self-expanding stent including a freely radially self-expanding fixation region in combination with a barrier region to inhibit tumor ingrowth.

Yet another object of the disclosure is to provide a stent that is in a reduced cross section state prior to implantation, and expands in the body to achieve a therapeutic state possessing larger cross section.

Yet another object is to provide an esophageal prosthesis deployable with reduced trauma to the patient, having more resistance to migration, and providing a barrier to tumor ingrowth.

Yet another object is to provide an esophageal prosthesis with controllable expansion regarding both rate and final cross section.

Yet another object is to provide an esophageal prosthesis with the proximal end of minimal diameter, and not engaged in preventing stent migration, so as not to affect the esophageal sphincter.

Yet another object is to provide an esophageal stent wherein the fixation region is detachable from the stent.

Yet another object is to provide a stent fixation region that does not rely on mechanical bonding to the inner lumen wall.

In particular, it is an object of the present application to provide a luminal stent that is resistant to migration, minimally damaging to the lumen lining, the contact with the lumen lining is adjustable, and the contact with the lumen lining follows any variations in the geometry or kinetics of the lumen lining.

The present invention is specifically directed to fixing or preventing the migration of a stent once it has been placed in a body lumen. And more specifically, to fixing region that employ a Wenzel-Cassie effect to provide a shear force in opposition to axial displacement of a stent.

The present disclosure the above needs and achieves other advantages which can be understood by the example of providing a stent for a lumen of the esophagus. The stent includes a tubular member and fixation regions located on or in contact with the tubular member. The fixation regions are configured to reduce migration and infolding of the stent during changes in geometry of the body lumen; for example, peristalsis.

Accordingly, the stent is capable of not only maintaining or even expanding a target area within a lumen but also mimicking the size and movement of the lumen. The present invention in some embodiments utilizes a modification of the stent's outer surface with microtextured features such as sinusoids, cylinders, ridges and other surfaces geometries to provide a non-mechanical bonding surface.

One embodiment of the present invention therefore relates to a radially-expandable implant for implantation in a bodily passageway, being at least partially expandable from an initial unexpanded state to an expanded state, having an outer surface with a geometric pattern covering said outer surface to minimize migration after implantation. It should be appreciated this pattern is extremely small in size, and in most cases undetectable by touch. However, the pattern presents a surface of microscopically and hierarchically arranged regions of varying hydrophilicity which has the unexpected effect of fixing a prosthetic within the aqueous and lubricious environment characteristic of most body lumens.

The stent is useable in various bodily passageways for implanting a stent, including the gastrointestinal tract (e.g., bile ducts, colon, duodenum), esophagus, trachea, urinary tract (e.g., urethra, prostate) and vasculature (e.g., aorta, coronary blood vessels, peripheral blood vessels, intracranial blood vessels).

According to one aspect of the present invention, the expandable cylindrical body of the stent may comprise more than one distal cuff in order to address the occurrence of a branch in the body vessel. The expandable cylindrical body being either modular or unibody in nature.

These and other features will be better understood through a study of the following detailed description and accompanying drawings.

DETAILED DESCRIPTION OF THE INVENTION

The following description is an exemplification of the principles of the present disclosure and is not intended to limit the disclosure to the particular embodiments illustrated herein.

Stents perform three functions: 1) stent or hold open a body lumen, 2) prevent ingrowth into a body lumen, and 3) anchor or fix functions 1 and 2 at a specific site within the body lumen.

Generally, there is no clinical requirement that the stent part responsible for the anti-migration or fixation feature should be fixed permanently to the stent part responsible for the radial force component. In other words, the anti-migration function and the stent function can be completely decoupled structurally. In this disclosure, the stent is considered to be all components of a lumen opening device implanted in a body.

Accordingly, the embodiments can be divided into three categories: 1) fixation regions integral to the stent, 2) fixation regions separable from the stent, and 3) fixation regions that are both separable and integral to the stent. In the third category, the fixation region provides the dual role of providing fixation and blocking ingrowth.

Textured Surface Fixation

The textured surfaces responsible for the fixation or gripping features of the stents of the present invention comprise textures that initially create Cassie and Wenzel states when exposed to a liquid environment in a mammalian body. These states evolve in situ, and their evolution analogues differ from typical Wenzel and Cassie states in that they involve a solid hydrophilic phase, a liquid hydrophobic phase, and a liquid hydrophilic phase or a solid hydrophobic phase, a liquid hydrophilic phase, and a liquid hydrophobic phase. In these modified Wenzel and Cassie states, the trapped phase analogous to the classical gaseous phase is the liquid hydrophobic phase. Alternatively, a trapped gaseous phase is preferentially replaced by a liquid hydrophobic phase.

The Cassie and Wenzel phenomena, occur when three phases are in contact with one another. In the body, the respective states lead to the formation and retention of an implant of a liquid hydrophobic film in the Cassie state and retention of tissue (containing lipids) in the Wenzel state. In a hybrid Cassie-Wenzel state, where one texture scale is Wenzel and the other is Cassie, the implant can be localizing to a tissue surface.

A scale of interaction is defined by the surface texture of the present stent surfaces, and is typically hierarchical, and characterized by at least two spatial scales, one on the order of micrometers (microns) and another on the order of 10 to 100 microns. The surface texture may induce one state with a large difference between preceding and receding contact angles (contact angle hysteresis), or alternatively another state with a small contact angle hysteresis. States of interest are known respectively as Wenzel and Cassie states. Each of the hierarchical spatial scales may induce separately a Wenzel or Cassie state, such that combinations are possible on a multiplicity of spatial scales. It is this combination of states that results in the surprising non-traumatic gripping feature of the present stents.

Examples of geometrical structures having scales of interaction include pillars, cubes, pyramids, or any feature with a typical overall size. For example, in the case of a cube, the scale of interaction would be the length of the cube. These surface structures, characterized by a scale of interaction are typically spaced apart, distance center to center, by a spatial frequency known as pitch. For example 4 micron squares with pitch 8 microns would mean the squares are separated on their surfaces by 4 microns. Typically the pitch is 1 to 10 times the scale of interaction. Also typically regarding hierarchical arrangement of different scales of interaction, the different scales of interaction and the pitch are 1 to 10 times smaller than the next hierarchical level. In many cases, one size of interaction is located on a large size of interaction. For example 1 micron pillars placed on the top surface of 10 micron pillars, with pitch 1 and 10 microns respectively.

These textures develop phenomena between hydrophobic and hydrophilic components of a mixture disposed on a surface interface. For example, the smaller interaction scales are hydrophobic and the larger interaction scales are hydrophilic. A hydrophobic surface attracts hydrophobic components in a interfacial mixture, and repels hydrophilic components, and conversely for hydrophilic surfaces.

The interaction of a solid textured surface with water in a gaseous environment is described by the Cassie-Baxter model. In this model, air is trapped in the microgrooves of a textured surface and water droplets rest on a compound surface comprising air and the tops of micro-protrusions. The importance of a fractal dimension between multiple scales of texture is well recognized and many approaches have been based on the fractal contribution, i.e., the dimensional relationship between different scales of texture. However, regardless of the material (organic or inorganic) used and geometric structure of the surface texture (particles, rod arrays, or pores), multiple scales of texture in combination with low surface energy has been required to obtain the so called superhydrophobic surfaces.

Superhydrophobicity is variously reported as a material exhibiting a contact angle with water that is greater than contact angles achievable with smooth but strongly hydrophobic materials. The consensus for the minimum contact angle for a superhydrophobic substance is 150 degrees, so in this context most of the embodiments of the present invention are not strictly superhydrophobic, although this option is not excluded. The reason for this is that a Wenzel-Cassie state lies in its hydrophobicity between non-textured surfaces and surface that generate a Cassie-Baxter interface. In optimizing the fixation of the stents of the present invention superhydrophobicity is just one aspect of a number of interesting texture controlled mechanisms, and in this context the contact angle is less important than the contact angle hysteresis.

A hydrophobic surface repels water. The hydrophobicity of a surface can be measured, for example, by determining the contact angle of a drop of water on a surface. The contact angle can be measured in a static state or in a dynamic state. A dynamic contact angle measurement can include determining an advancing contact angle or a receding contact angle with respect to an adherent species such as a water drop. A hydrophobic surface having a small difference between advancing and receding contact angles (i.e., low contact angle hysteresis) results in surfaces with low resistance to in plane translation (low adherence). Water can travel across a surface having low contact angle hysteresis more readily than across a surface having a high contact angle hysteresis, thus the magnitude of the contact angle hysteresis can be equated with the amount of energy needed to move a substance.

A high surface area is achieved by superimposing multiple structures one on top of the other in superposition. When these multiple structures are sufficiently different in dimension then the superposition of these structures is referred to as a hierarchical structure or pattern. A subset of surfaces useful in the present invention are characterized as superhydrophobic.

Surface textures useful in the stents disclosed herein provide a gripping or fixation region when in contact with a body lumen, such as a lumen of an esophagus. The surface texture can comprise at least one class of hydrophobic regions on at least one spatial interaction dimension, and at least one class of hydrophilic regions on one or more other spatial interaction dimensions, wherein the ratio of any two spatial dimensions is greater than 2.

One embodiment of a surface texture useful in the present stents is a biomimetic of the natural rose pattern. Referring to FIG. 1, the pattern 100 comprises three structures: 1) a two-dimensional sinusoidal pattern 102, 2) a first column pattern 104, and 3) a second column pattern 106 combined with a flute pattern 108 disposed on second column 106. These structures have characteristic dimensions. For example the amplitude 110 and pitch 112 of the sinusoidal pattern 102 is in the range of 50 to 500 microns or larger. The height 114, diameter 116 and pitch 118 of the first column pattern is in the range 20-50 microns. The height 120, diameter 122 and pitch 124 of the second column pattern as well as the height 126 and pitch 128 of the flutes are in the range of 5-20 microns.

Fixation Integral to the Stent

In accordance with one embodiment of the present invention, the stent can be manufactured by utilizing an injection molding process. By utilizing this process, a particular surface texture of the stent can be controlled by cutting the inverse surface texture pattern into the inner diameter of the mold. The inner surface of the mold can contain any of various geometrical patterns arranged hierarchically and possessing different spatial dimensions such as sinusoids, columns, pyramids or flutes, as shown in FIG. 1.

In some embodiments, low profile geometries on the exterior wall of the stent will minimize migration while preventing tissue damage in situ or upon removal. Additionally, these structures, since they are arranged hierarchically allow fluids to flow between the stent and body lumen. For example, fluids from either the pancreatic duct or cystic duct can pass between the wall of the bile duct and the outer surface of the stent, should the stent pass over these ducts.

In one embodiment, the invention comprises a stent and, more preferably, a stent suited for placement within the gastrointestinal (GI) tract of an animal or a human. In a further embodiment, the GI tract comprises the esophagus, the pancreatic duct, cystic duct or common bile duct. In yet a further embodiment, the outer surface of the implant comprises at least one surface texture that provides a fixation region to assist in limiting the potential migration of the implant within the body lumen. In addition to its use as an esophageal prosthetic, the present invention may be used in any bodily vessel, such as in the coronary or peripheral vasculature, esophagus, trachea, bronchi, colon, biliary tract, urinary tract, prostate, brain, as well as in a variety of other applications in the body.

Figure 1A:
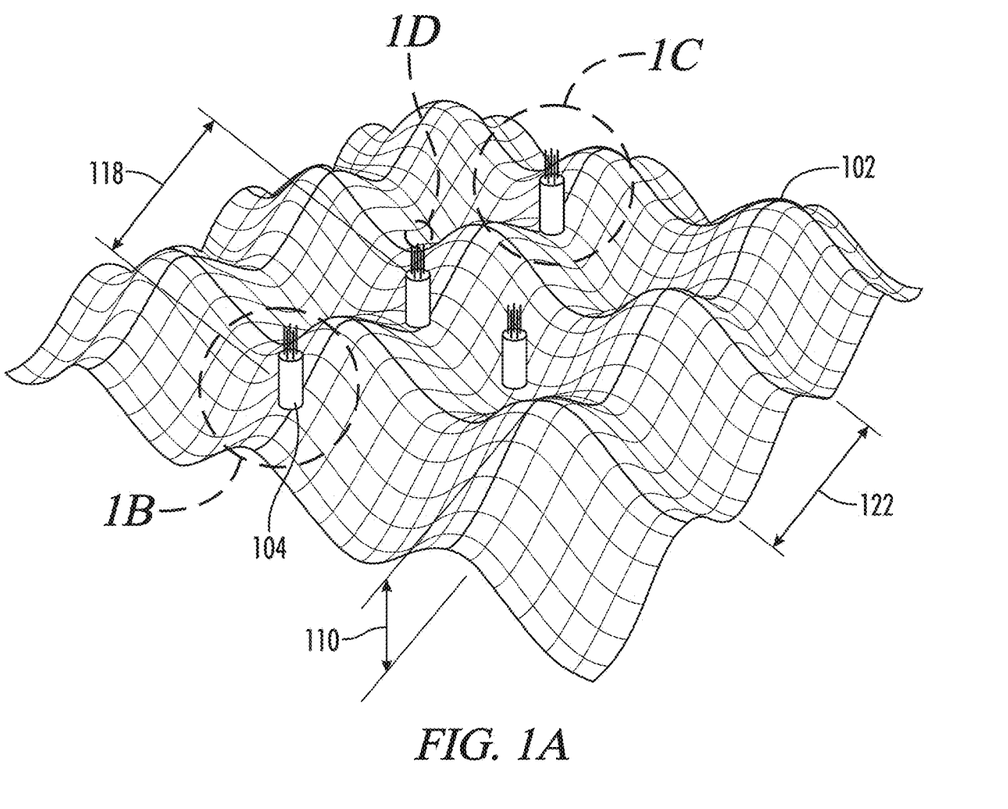
FIG. 1A-1D is a schematic diagram of an exemplary textured surface useful in the stents of the present disclosure.
Figure 1B:
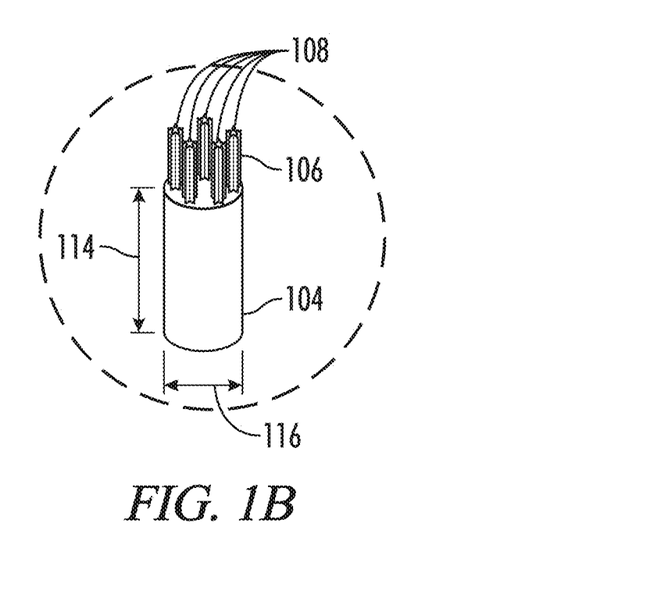
Figure 1C:
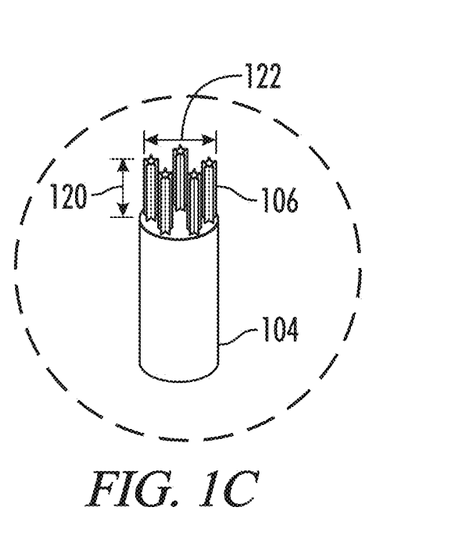
Figure 1D:
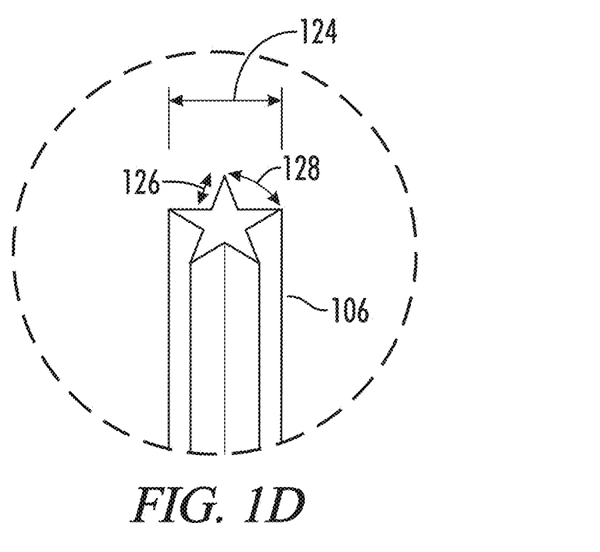
Figure 2A:
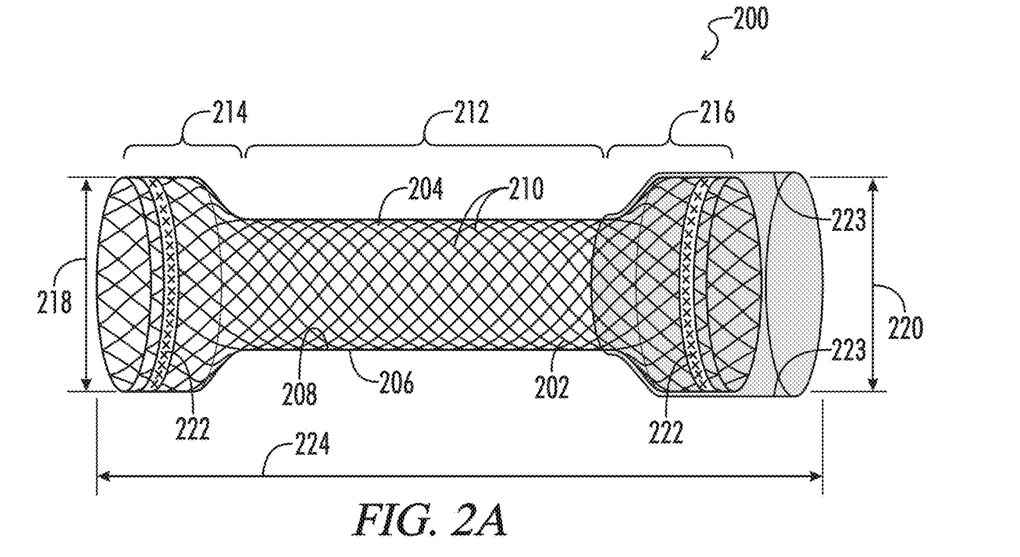
FIG. 2A depicts an exemplary stent having a microtextured surface region.

FIG. 2A depicts stent 200 of the present invention. In one embodiment, stent 200 includes a stent body 202 having an axial length 224. The stent 200 assumes the normal or relaxed configuration, as depicted in FIG. 2, when it is not subject to any external load or stress. The stent body 200 may be partly or fully covered with an elastomeric membrane or film 204. The elastomeric film 204 is defined by an exterior surface 206 and an inner surface 208. The film may be disposed axially along the stent to cover substantially the entirety of the axial length of the stent. Stent 200 comprises an open weave construction of mesh segments 210. Mesh segments 210 may be metal wire or a polymeric mesh, and provide a flexible stent structure in some embodiments. Wires or segments 210 may be paired and helically wound.

Stent 200 includes several regions, including an intermediate region 212, a distal end cuff region 214 and a proximal end cuff region 216. The distal end cuff region 214 and the proximal end cuff region 216 may be shaped so as to have a wider cross-section than intermediate region 212, for example, which may be useful as an esophageal prosthetic device. Distal end cuff region 214 and proximal end cuff region 216 may include flares or dilated regions having cross sections 218 and 220. The cuff region and/or the flares have a diameter that is larger than the diameter of the intermediate region and aid in fixation of the stent when inserted in a body lumen.

The stent 200 further includes a surface texture disposed on a portion thereof, the surface texture providing a fixation region of the stent. As depicted in FIG. 2A, the surface texture 222 may be disposed on the flare regions 218 and 220 in some embodiments. The surface texture 222 can be a three dimensional geometric structure depicted in FIG. 1, and may be integrally formed with the elastomeric film 204. The surface texture 222 provides an anti-migration effect to the prosthesis 200.

This embodiment provides improved stent fixation and is particularly effective in resisting either proximal or distal migration of the stent 200 upon insertion into a body lumen. Flared cuffs 218, 220 may be designed with flexibility to readily conform to changes in the body lumen wall during the transmittal of bodily fluid or food. Alternatively, the present invention also envisions a stent body having no flared end, or including one flared end.

In some embodiments, each end of the stent comprises a fixation region. In some embodiments, the fixation region comprises an inflatable annulus. In other embodiments, the textured region comprises an elastic polymeric torus.

Figure 2B:
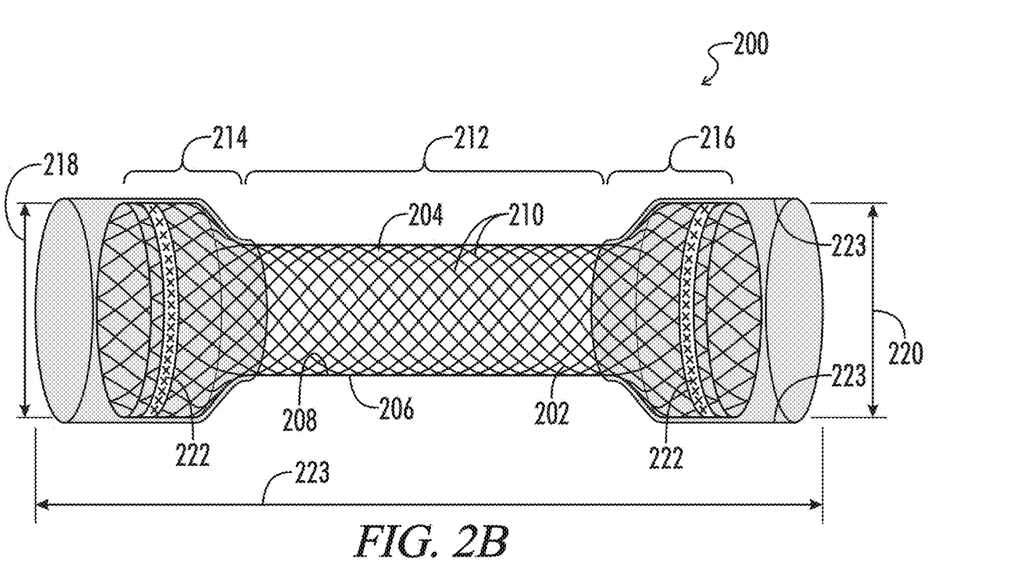
FIG. 2B depicts the stent of FIG. 2A further comprising a delivery sleeve.

FIG. 2B depicts an embodiment of stent 200 having a delivery sleeve 223 disposed around the exterior of stent body 200. The delivery sleeve may be disposed around any area of the stent 200, including at least one of the intermediate region 212, distal end cuff region 214 and proximal end cuff region 216. The delivery sleeve advantageously aids in the positioning and deployment of the stent within the body lumen.

Generally, the exterior surface 206 of the stent 200 may be designed to be fairly smooth. A surface texture 222, such as a three dimensional geometric structure depicted in FIG. 1 may be integrally formed with the elastomeric film 204. The surface texture 222 provides an anti-migration effect to the prosthesis 200.

As depicted in FIG. 1, surface texture 222 may be a three-dimensional geometric structure containing a relief feature such as columns, sinusoids, or flutes. However, the surface texture 222 may encompass any projection or indents of shapes or other complex geometries which comprise hierarchical and alternating regions of differing hydrophilicity over the exterior surface 206. When formed with the surface texture 222 disposed over the exterior surface 206, the stent body 200 is given a wet surface gripping functionality over all or a portion of the surface 206, which act as fixation regions between the stent body 200 and the body lumen into which the stent body 200 is disposed.

The surface texture 222 may be configured to accommodate various tolerances in delivery systems which in some embodiments are to be used with the stent body 200. For instance, a stent body 200 is depicted in its relaxed or normal configuration in FIG. 2. As depicted, the intermediate region 212 may have a diameter of about 15-20 mm, and the cuff of the proximal region 214 and/or the cuff of the distal end region 216 may have a diameter of about 25-28 mm. In this particular embodiment, the wires 210 may have a diameter of about 0.22 mm or less. The three-dimensional structure 222 may preferably have a cross section of less than approximately 1 mm. This tolerance ensures that the overall diameter increase of the delivery device is kept, for instance, less than 2 mm (assuming one three-dimensional structure 222 wraps around the stent). However, the present invention is not limited by the exemplary dimension tolerance. The total diameter may vary according to usage of the particular delivery device in a particular vessel. For instance, the dimensional tolerance for esophageal stent may be different from a coronary stent.

Figure 3:
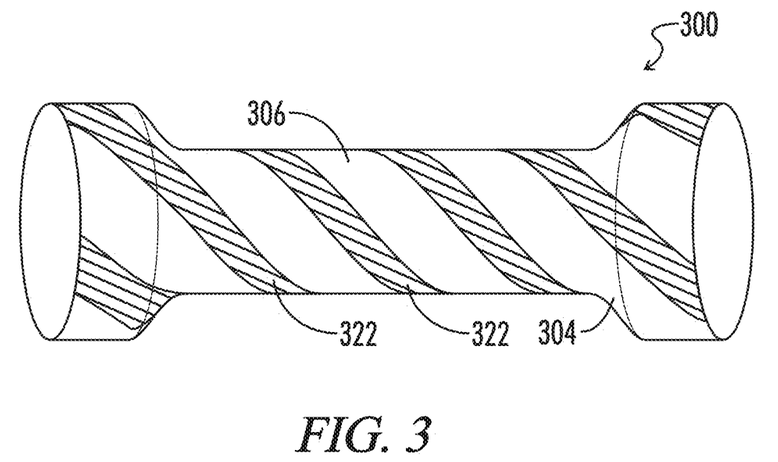
FIG. 3 is alternative embodiment of a stent having a microtextured surface region.

FIG. 3 depicts yet another embodiment of the present invention in which the surface texture layer 322 is not integrally formed with the elastomeric membrane 304. As depicted in FIG. 3, a thin discrete layer may be disposed on the exterior surface 306. In one particular embodiment, the anti-migration structure layer 322 forms a pattern helically expanded about the exterior surface 304 of the intraluminal prosthesis 300. According to one embodiment of the invention, the surface texture 322 may be formed from the same material from the elastomeric membrane 304 is formed. In some embodiments, the surface texture 322 may be in the form of bands that span across a common longitudinal axis of the stent body 300.

In another embodiment, the stent body 300 may be provided with the first set of anti-migration bands comprising surface texture 322 having a common direction of winding but circumferentially displaced relative to each other. In this embodiment, the first set of anti-migration bands comprising surface texture 322 may be configured to cross a second set of anti-migration bands also circumferentially displaced relative to each other but winding in substantially opposite direction. In this embodiment, the stent body 300 is sufficiently configured to have anti-migration properties, as provided by the anti-migration bands. The directions of the bands for the present invention are not limited by the above examples, and also may extend lengthwise or perpendicular to the longitudinal axis. Further, the bands may change direction at random locations, for example, they may be curved or wavy at random locations along stent 300.

The device 300 of the present invention may include surface textures 322 provided as bands configured to flex along certain selective dimensions. For instance, the surface texture band 322 may include an anti-migration structure that is flexible in a radially outward direction of the stent body 300. In addition, the surface texture 322 may be rigid in the longitudinal direction at certain locations.

Various methods of forming the stents are provided herein. In one embodiment, during the fabrication process of the stent body 200, surface texture 222 may be added to the wires 210 after the outer surface 206 is disposed on the wires 210. In an alternate embodiment, the surface texture 222 may be provided as a layer formed integrally with the wires 210. Instead of the layer completely wrapping over exterior surface 206, bands of the surface texture 222 may be interwoven with the wires 210. In this embodiment, the surface texture 222 may partially or wholly substitute the elastic membrane 204.

Figure 4:
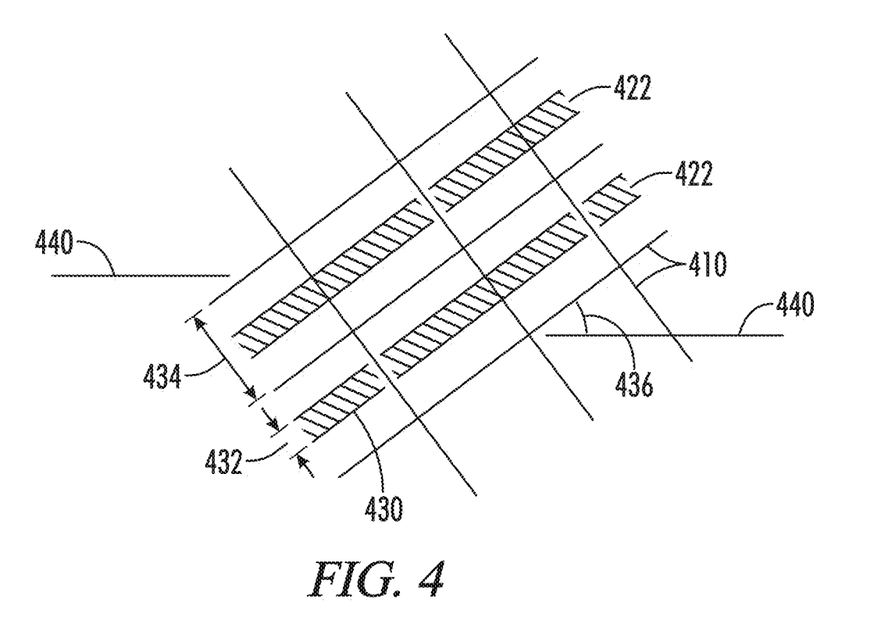
FIG. 4 is a schematic of an embodiment where the textured regions are provided as bands.

FIG. 4 depicts a portion of a stent body 200. The surface texture 422 may be provided as anti migration bands 430 having smaller width 432 than the distance 434 between wires 410. In an alternate embodiment, the bands 436 may along exposed portions 438 have a width 440 larger than the distance 434 between wires 410. Further, the stent 400 may be configured with a variety of bands 422 of different widths.

Yet another advantage of the surface texture being provided as anti-migration bands 430 disposed on the elastomeric membrane is that it may provide structural reinforcement along the stent body. This reinforcement may enable the wires 410 to be constructed with a reduced angle. As used herein, the angles between the wires 410 is measured based on their incline deviation from the axis 440 of the stent.

In prior stents, an angle 436 of 45 degrees from the axis 440 may have been considered a lower practical limit for the angle of a mesh or open weave wire stent 200. Employing the present invention, however, may enable a reduction of the braid angle to as low as 20 degrees from the axis 440. The advantage of a lower angle for the wires 410 follows from the fact that the angle may contribute to the ratio of stent axial shortening to its radial increase structure. As the stent expands, either through use of self-expanding materials or through the assistance of a balloon, a lower angle facilitates greater radial expansion of the stent body 200. With a reduced braid angle, upon expansion, there may be less axial shortening for a given radial expansion. Due to the reduced axial shortening, the stent body 200 may be more accurately positioned within the body lumens during its deployment. Thus, the profile of a surface texture 422, in combination with the stent 200, may resist the extraneous stretching and assist in the precise positioning of the stent inside a body lumen.

There are a multiplicity of arrangements of the anti-migration layer that are clinically preferred, depending upon the application. The possibilities are: full coverage of the stent, spiral patterns formed using strips, checkerboard pattern of squares or circles located on the crossing points of the wires, and mainly on the end regions (flared) and in segments or a continuous band.

In general, coating of the device with an elastomeric membrane is designed to enhance lumen patency. In addition, the tubular coating may resist tumor ingrowth. The thickness of the elastomeric membrane may be in the range of 0.075-0.25 mm. However, such elastomeric membrane may also be up to a range of 0.75-1.00 mm. In some embodiments, the elastomeric membrane may include a silicone film layer. The elastomeric membrane 204 may be disposed onto the outer surface of the stent body 200 by any desired means, including by placing the elastomeric membrane onto the surface, by extruding the elastomeric membrane onto the outer surface, or by dipping or spraying the elastomeric membrane onto the outer surface.

The elastomeric membrane of the prosthesis may also be formed of polytetrafluoroethylene (PTFE/ePTFE). Considered alone, the coating should provide an effective barrier to tissue ingrowth. In addition, the elastomeric membrane may be elastic, and thus may radially expand like the remainder of stent body. Thus, silicone construction, in general, may be engineered to exert constant, gentle pressure to help adapt to normal luminal patency, for instance of esophageal peristalsis as its smooth inner surface helps facilitate passage of fluid. Optionally, the ends of the prosthesis may also be reinforced by continuous polymeric film to help resist hyperplasia.

All of the components of the intraluminal device should be made of biocompatible materials, including metals or polymeric materials. Any materials may be used in the forming of these elements. In one embodiment, the elastomeric membrane preferably includes silicone, but other materials having elastomeric and biocompatible characteristics are also envisioned by the present invention. By way of example and not limiting the invention in any manner, other materials for any or all of the components of the device may include polyurethane, polyethylene, polytetrafluoroethylene, or expanded polytetrafluoroethylene, polyolefins such as high density polyethylene and polypropylene, polyolefin copolymers and terpolymers, polyethylene terephthalate, polyesters, polyamides, polyurethaneureas and polycarbonates, polyvinyl acetate, thermoplastic elastomers including polyether-polyester block copolymers, polyvinyl chloride, polystyrene, polyacrylate, polymethacrylate, polyacrylonitrile, polyacrylamide, silicone resins, combinations and copolymers thereof, and the like.

Other useful coating materials include any suitable biocompatible coating. Non-limiting examples of suitable coatings include hydrophilic materials, hydrogels, and the like. Useful hydrophilic coating materials include, but are not limited to, alkylene glycols, alkoxy polyalkylene glycols such as methoxypolyethylene oxide, polyoxyalkylene glycols such as polyethylene oxide and its copolymers, polyethylene oxide/polypropylene oxide copolymers, polyalkylene oxide-modified polydimethylsiloxanes, polyphosphazenes, poly(-ethyl-2-oxazoline), homopolymers and copolymers of (meth) acrylic acid, poly(acrylic acid), copolymers of maleic anhydride including copolymers of methylvinyl ether and maleic acid, pyrrolidones including poly(vinylpyrrolidone) and its derivatives, homopolymers and copolymers of vinyl pyrrolidone, poly (vinylsulfonic acid), acryl amides including poly(N-alkyl acrylamide), poly(vinyl alcohol), poly(ethyleneimine), poly (carboxylic acids), methyl cellulose, carboxymethylcellulose, hydroxypropyl cellulose, polyvinyl sulfonic acid, water soluble nylons, heparin, dextran, modified dextran, hydroxylated chitin, chondroitin sulphate, lecithin, hyaluronan, combinations and copolymers thereof, and the like.

Other non-limiting examples of suitable hydrogels include hydroxyethyl acrylate or hydroxyethyl(meth)acrylates; polyethylene maleic anhydride, combinations and copolymers thereof, and the like.

Other useful synthetic biocompatible polymeric materials include, but are not limited to, polyesters, including poly methyl acetates, naphthalene dicarboxylate derivatives, and silks. The polymeric materials may further include a metallic, a glass, ceramic or carbon constituent or fiber. Useful and non limiting examples of bioabsorbable or biodegradable polymeric materials include poly(L-lactide), poly(D,L-lactide), poly(glycolide), poly(L-lactide-co-D,L-lactide), poly(L-lactide-co-glycolide), poly(D,L-lactide-co-glycolide) (PLA/PGA), poly(glycolide-co-trimethylene carbonate) (PGA/PTMC), polydioxanone, Polycaprolactone, polyhydroxybutyrate, poly(phosphazene) poly(D,L-lactide-co-caprolactone), poly(glycolide-co-caprolactone), poly (phosphate ester) and the like. Some other materials which may be used as the filament include, but are not limited to polyether ether ketone, fluorinated ethylene propylene, and polyimide, polybutylene terephthalate, polyurethane rubber, and silicone rubber.

Any component of the prosthetic device, and particularly the anti-migration structure layer, may also include a therapeutic agent that may be released into the body. Useful therapeutic agents or drugs include but not limited to, anti-platelets, anti-thrombins, anti-tumor drugs, anti-hyperplasia agents, anti-plaque building agents, cytostatic agents, and anti-proliferative agents, or other drugs for a specific purpose. This may also include agents for gene therapy. The therapeutic agent or drug is preferably selected from the group of therapeutic agents or drugs consisting of urokinase, dextro phenylalanine proline arginine chloromethylketone, enoxaparin, angiopeptin, acetylsalicylic acid, paclitaxel, 5-fluorouracil, cisplatin, vinblastine, vincristine, sulfasalazine, mesalamine, sodium heparin, low molecular weight heparin, hirudin, prostacyclin and prostacyclin analogues, dextran, glycoprotein IIb/IIIa platelet membrane receptor antibody, recombinant hirudin, thrombin inhibitor, calcium channel blockers, colchicine, fibroblast growth factor antagonists, fish oil, omega 3-fatty acid, histamine antagonists, HMG-CoA reductase inhibitor, methotrexate, monoclonal antibodies, nitroprusside, phosphodiesterase inhibitors, prostaglandin inhibitor, suramin, serotonin blockers, steroids, thiol protease inhibitors, triazolopyrimidine and other PDGF antagonists, alpha-interferon and genetically engineered epithelial cells, and combinations thereof. The foregoing list of therapeutic agents is provided by way of example and is not meant to be limiting, as other therapeutic agents and drugs may be developed which are equally applicable for use with the present invention.

Stents of the present disclosure may be manufactured from a mold comprising a top portion and a bottom portion. The top portion may comprise an inner and outer surface, wherein the inner surface may be adapted to receiving material for the manufacture of the stent according to the present invention. The stent may be formed as a hollow structure, which may be etched, or may be formed as a coiled structure resembling a coil spring. U.S. patent application Ser. No. 10/683,314, filed Oct. 10, 2003, disclose suitable materials and geometries for stents.

In another alternate method of manufacture, the stent may be formed by molding the exterior surface modification onto a separate layer of material, such as for example a non-textile material. As used herein, the term "non-textile" and its variants refer to a material formed by casting, molding, spinning or extruding techniques to the exclusion of typical textile forming techniques, such as braiding, weaving, knitting and the like. Non limiting examples of useful polymeric materials for the non-textile polymeric graft portions include polyesters, polypropylenes, polyethylenes, polyurethanes, polynaphthalenes, polytetrafluoroethylenes, expanded polytetrafluoroethylene, silicone, and combinations and copolymers thereof. Desirably, the polymeric material polytetrafluoroethylene, including expanded polytetrafluoroethylene.

A stent can be formed in a variety of configurations and of a variety materials known to one skilled in the art. In particular, conventional esophageal stents can be used or readily modified for use in the present invention. Such stents can be of the non-expanding or expanding variety, including those typically used in addressing problems of progressive dysphagia associated with esophageal cancer. Expanding stents include those that are deformable and that are typically expanded using, e.g., a balloon catheter, as well as those that are resilient in nature and that can be delivered in a compressed state and which can self-expand to their original state. Preferably, the stents are of the radially self-expanding variety for ease of deployment in the esophagus. Typically, such stents are made of stainless steel or nitinol (nickel-titanium alloy) and formed into e.g. knitted wire tube, tubular mesh, coiled spring, and like configurations. Suitable self-expanding esophageal metal stents include those sold under the brand names Esophacoil™ (Medtronic/Instent, Eden Prairie, Minn.), Ultraflex™ (Boston Scientific/Microvasive, Natick, Mass.), Wall Stent™ (Boston Scientific/Microvasive, Natick, Mass.), and Z-stent™ (Wilson-Cook, Winston-Salem, N.C.). Additional examples of such stents include those described in U.S. Pat. Nos. 5,876,448 and 6,248,058, each of which is incorporated herein by reference in its entirety. Length and diameter of the stent can usually range from 6-15 cm (length) and 16-22 mm (diameter) for most applications. The stents may further be coated, either partially or completely, with e.g. a polymeric film such as silicone.

Any stent can have a covering and the coverings are thus not limited to nitinol stents. Moreover, the stent need not be covered whatsoever, may be partially covered or may be fully covered. The stent may also have a covering on the inside, the outside or both.

Other suitable covering materials can be employed as well. Examples of other suitable covering materials include, but are not limited to, polyethylene, polypropylene, polyvinyl chloride, polytetrafluoroethylene, including expanded polytetrafluoroethylene, fluorinated ethylene propylene, fluorinated ethylene propylene, polyvinyl acetate, polystyrene, poly(ethylene terephthalate), naphthalene, dicarboxylate derivatives, such as polyethylene naphthalate, polybutylene naphthalate, polytrimethylene naphthalate and trimethylenediol naphthalate, polyurethane, polyurea, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof.

Alternatively, the stent may have a braided construction with a flared proximal end. In this embodiment, the stent is an esophageal stent. A stent may be formed of any suitable stent material including metallic and non-metallic materials as well as shape memory materials. Examples of suitable materials include, but are not limited to, shape memory alloys such as Nitinol, other metallic materials such as stainless steel, tantalum, titanium, nickel-chrome, or cobalt-chromium alloys such as those sold under the tradename of Elgiloy®. A stent may have a flared distal end or flared proximal and distal ends as well.

Hydrogel Cushioned Stents

Figure 5:
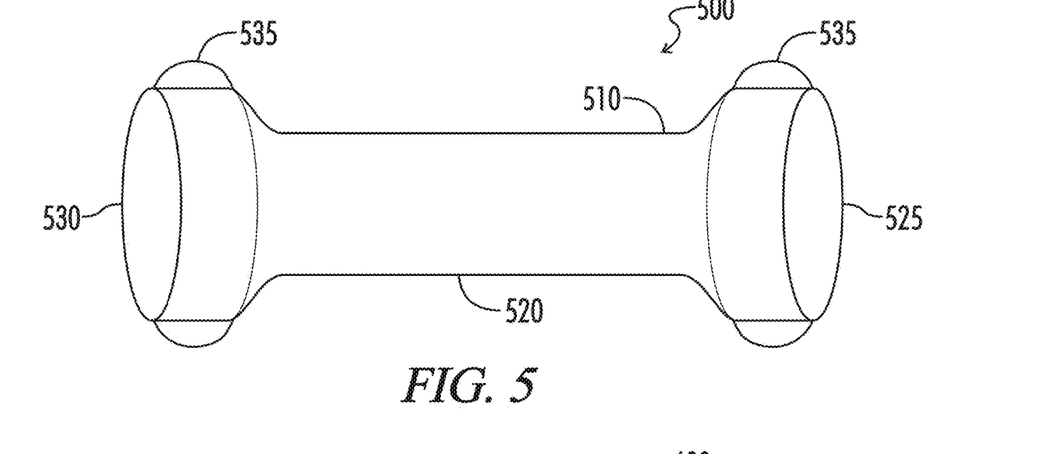
FIG. 5 depicts a stent having a hydrogel coating disposed on a cuffed or flared end of the stent.

In FIG. 5, a hydrogel coated stent 500 is shown in its expanded form. The hydrogel coated stent 510 comprises a proximal cuff or flare 525, a main elongated body 520, a distal cuff or flare 530. A hydrophilic polyurethane hydrogel 535 is disposed about at least one of the proximal 525 and distal cuffs 530 of the stent 510. Preferably, the proximal cuff 525 includes a hydrophilic polyurethane hydrogel. According to another aspect of the present disclosure, both cuffs 525 and 530 comprise the polyurethane hydrogel.

When initially inserted into the body vessel, each of the cuffs 525, 530 and the elongated body 520 are similar in diameter and allow for continued fluid flow around the exterior of the stent 510. However, upon exposure to an aqueous environment (i.e., bodily fluids) the polyurethane hydrogel expands so that the outer diameter of the cuffs 525, 530 increases. This increase in diameter causes the cuffs 525, 530 to exert a sealing force against the wall of the body vessel. This sealing force stops the bodily fluid from flowing between the cuffs 525, 530 and the vessel wall, thereby, forcing all of the fluid flow to enter and exit through the stent 510.

The use of a hydrophilic polyurethane hydrogel can potentially reduce the incidence of encrustation and the occurrence of a complicating infection. However, if this polymer layer is a polyurethane hydrogel, the polymer layer will enlarge or swell when exposed to an aqueous environment, thereby, allowing the struts of the stent-graft to bend more freely without kinking.

The polyurethane hydrogel layer represents a 3-dimensional network of cross-linked hydrophilic macromolecules that can swell and absorb about 20 to 90 percent by weight of water. The hydrogel layer may be applied as or onto the cuff of a stent-graft by coating, adhesive bonding, lamination, extrusion, or molding. The application method used is selected to provide a layer of the hydrogel having a substantially uniform thickness.

The stent may comprise an expandable or inflatable structure embedded within a polymeric matrix or a solid polymeric matrix. In both cases, the polyurethane hydrogel may be applied as a strip or band disposed around the outer surface of the cuff, such as a torus shape or an annulus.

After the hydrogel is disposed around the cuff of a stent, it may be dried by any method known in the art, including but not limited to conduction drying, convection drying, hot air impingement, steam treatment, infrared irradiation, ultraviolet irradiation, and microwave irradiation. Preferably, the hydrogel coating is dried by the application of thermal energy.

Drying the hydrogel causes it to dimensionally shrink. A stent whose hydrogel cuff is dried can be made to shrink to a cross section ready for insertion into a body vessel. In this condition, the hydrogel cuff can take about the same diameter as the elongated body 520 of the stent 510. In some cases the act of drying the polyurethane gel will cause the stent to be in collapsed state. If the hydrogel is formed around a mesh, the gel will expand only in the direction perpendicular to the mesh. The shape and ratio of polyurethane to water is predetermined at the moment of polymerization.

The migration resistant surface texture can be applied to the hydrogel or elsewhere on the stent. If applied to the hydrogel, the surface texture can be applied either in the hydrogel dry state or wet state. In either case, the surface texture can be applied as an elastomeric layer or a segmented layer, or formed in the hydrogel itself.

Fixation Separate from the Stent

In some cases, once the stent is deployed, the position of the stent may shift relative to its position in the body lumen prior to deployment. After the stent is deployed, it can be difficult to reposition the stent. In some cases, re-positioning of the stent can be facilitated by decoupling the stenting function from the fixation function.

Figure 6:
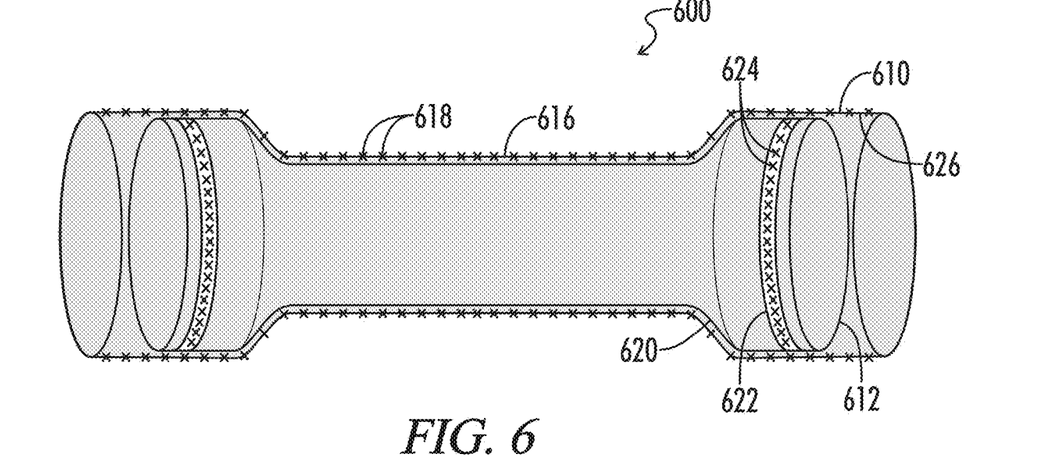
FIG. 6 depicts a two-part stent comprising a stent and a fixation sleeve.

Referring to FIG. 6, a two-part stent 610 comprises a conventional wire stent 612 and fixation sleeve 614. Stent 610 is shown in its deployed state. To deliver the stent, stent 610 is collapsed. Once deployed, outer sleeve surface 616 with surface texture 618 engages the inner wall of the body lumen. On initial deployment, wire stent 612 can easily be relocated within sleeve 614 without moving the sleeve 614 relative to the body lumen.

Wire stent 612 comprises outer surface 620 and optionally a fixation region 624. Alternatively, in the case where fixation region 624 is absent, wire stent 612 can be fixed to sleeve 614 via suture, staple or the like.

Preferably, fixation region 624 is a surface texture 622 coated with a water soluble material such that initially surface texture 622 is smooth. Optionally, a second coated surface texture may be placed on the inner surface 626 of sleeve 614. The coating may be any material used in the pharmaceutical industry to delay release of a drug.

After a predetermined time, the coating dissolves either through irrigation or due to body fluids present in the body lumen. Upon dissolution of the coating, wire stent 612 fixes to sleeve 614, and sleeve 614 is fixed to the inner wall of the body lumen, thus fixing stent 610 within the body lumen.

Fixation Both Separate and Integral to the Stent

In yet another embodiment, the fixation region can be woven into the stent in a relatively loose configuration, which allows repositioning of the stent without repositioning the fixation region. After deployment, the loose configuration can be tightened or fixed.

Figure 7:
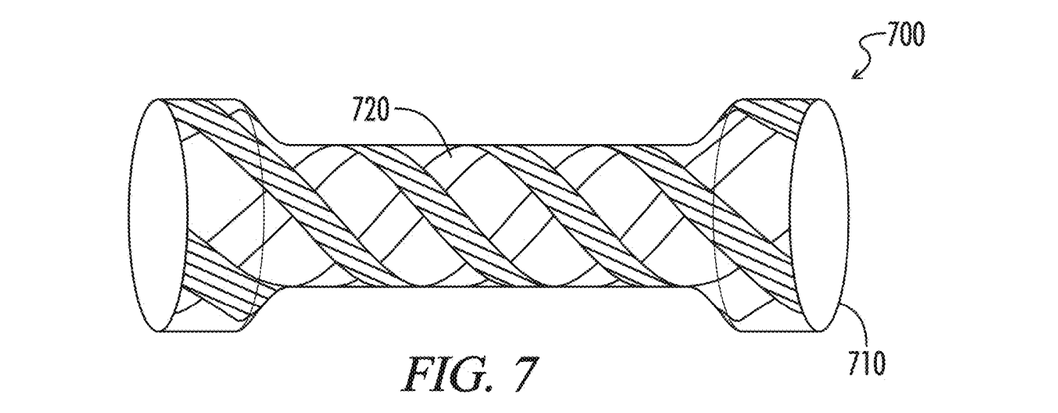
FIG. 7 depicts a stent having a fixation region woven into the stent.

In one particular embodiment shown in FIG. 7, stent 700 comprises stenting body 710 and movable anchoring element 720 is in the form of a strip of patterned silicone. Stent 710 may be coiled or patterned as a braided or woven open network of wires, fibers or filaments interwoven in a braided pattern to form a tubular stent 700, In this embodiment, the movable anchoring element 720 may extend in the direction of the longitudinal axis of the stent and can be interwoven in the braided construction of the stent 710. The anchoring elements 720 may be fixed at one end, both ends, or at some point in between the distal and proximal portions of the stent. The anchoring element may comprise a surface texture as described herein.

Any number of strips can be employed. Suitably, a minimum of two strips are positioned symmetrically about the circumference of the stent 700 to provide uniform anchoring in a body lumen.

Additionally, a single circumferential ring of anchoring elements may be positioned in the middle of the stent to prevent stent "walking" which may occur if anchoring elements are positioned at both ends of the stent.

Figure 8:
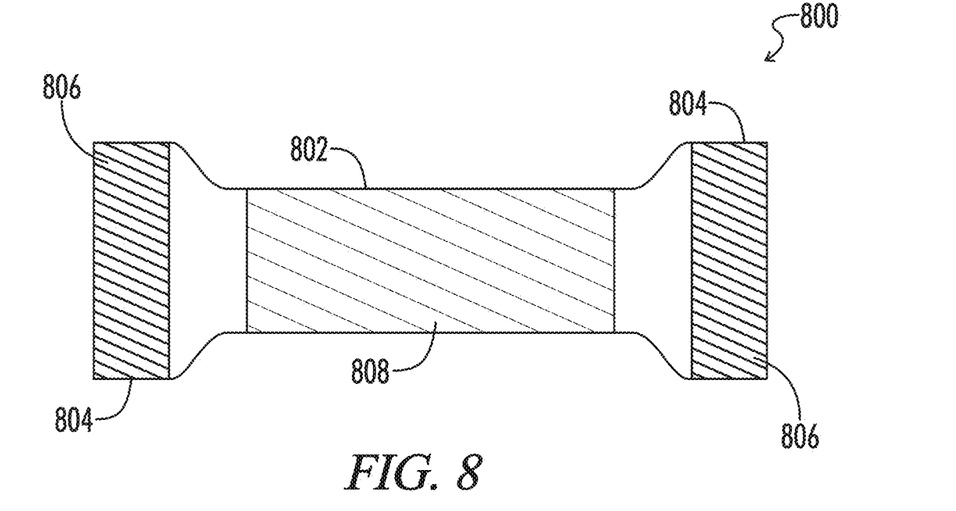
FIG. 8 depicts a stent having a fixation region disposed on flared regions, and further having a lubricious region on the stent body. In this embodiment, the spring constant of the stent body may be selected to match the spring constant of the esophagus in which it is inserted.

With reference to FIG. 8, an esophageal stent 800 comprises stent body 802 and dilated regions 804 where a surface texture 806 is disposed thereon, thereby providing a fixation region. A lubricious region 808 is disposed on the middle of the stent body 802. The spring constant of the stent body 802 may be designed to match the spring constant of a target esophagus.

Figure 9:
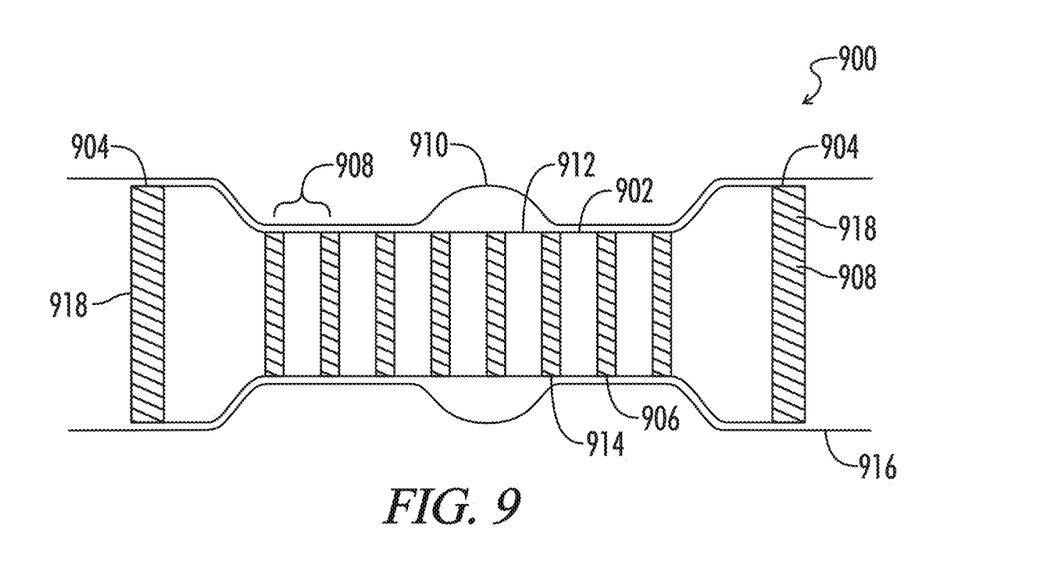
FIG. 9 depicts a stent having a plurality of surface textures regions disposed annularly about the stent body with a selected spatial periodicity alternating with slip regions.

With reference to FIG. 9, an esophageal stent 900 comprises stent body 902 and dilated regions 904 where a surface texture 906 is provided as an annular band and disposed over the stent body 902 with a particular spatial periodicity. In this embodiment, the wavelength of the target esophageal peristaltic motion is known. For example, for the adult human esophagus the peristaltic wavelength is approximately 5 cm. When stent 900 is placed in a human esophagus, the surface texture 906 is placed at ½ wavelength intervals 908, such that esophageal peristaltic wave 910 is alternatingly slipping in regions 912 and gripping the esophageal wall in regions 914. This arrangement of grip surfaces allows the passage of the esophageal peristaltic wave without displacement of esophageal stent 900 relative to the esophagus 916. Alternatively, the spacing 908 may be one wavelength. Alternatively, surface textures 918 may be disposed on cuff or flared regions 904.

The slip regions of FIGS. 8 and 9 may comprise a lubricious membrane, such as silicone, or a gel, such as a hydrogel.

Figure 10:
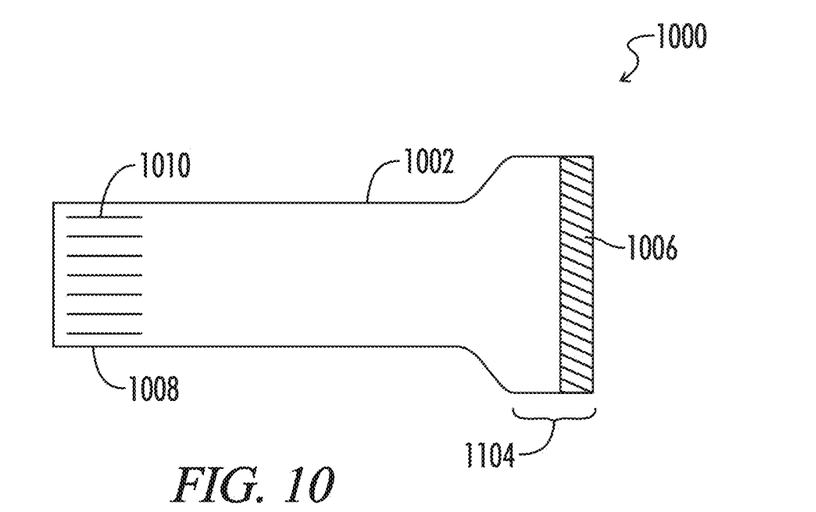
FIG. 10 depicts an embodiment of a stent wherein a first end comprises a cuffed or flared region comprising a surface texture and second end that is free floating within a body lumen. The free end may comprises lubricious ribs axially oriented.

With reference to FIG. 10, an esophageal stent 1000 comprises a stent body 1002 and one flared or cuff region 1004 where surface texture 1006 is disposed over the stent body 1002. In this embodiment, one end 1008 is free floating within an esophagus. Optionally, end 1008 may be configured with lubricious ribs 1010 oriented axially, such that the esophagus is induced to slip axially without stent end 1008 displacement. Ribs 1010 may be of sufficient height to prevent rotational displacement of stent end 1008. Optionally, hydrogels may be disposed on ribs 1010.

Figure 11:
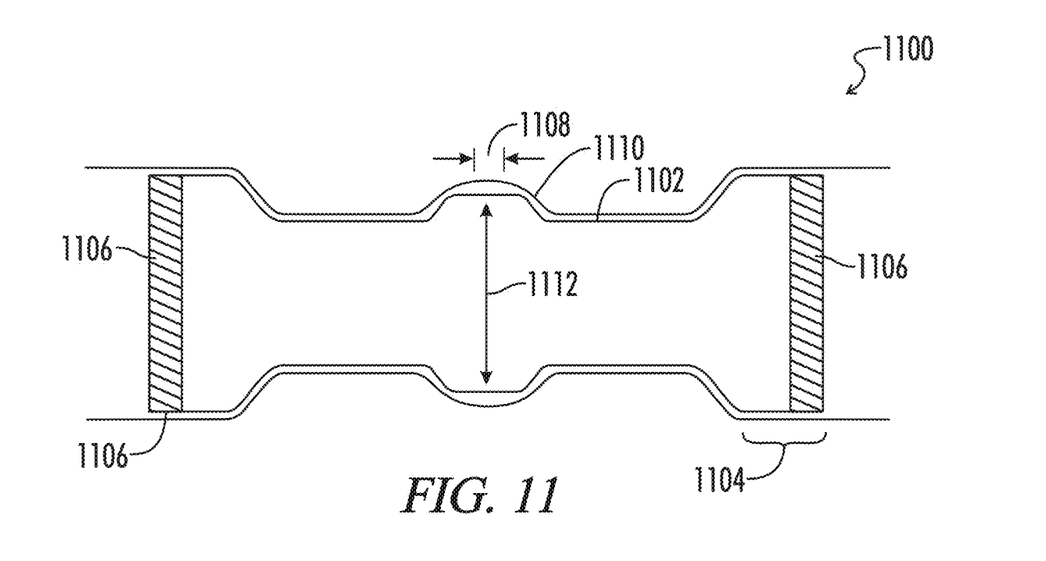
FIG. 11 depicts an esophageal stent comprising a surface textured region. The stent body advantageously dilates in response to a peristaltic wave from a body lumen.

With reference to FIG. 11, an esophageal stent 1100 comprises a stent body 1102 and cuff or flare regions 1104 where surface texture 1106 is disposed over the stent body 1102. Stent body 1102 when compressed in direction 1108 by peristaltic wave 1110, stent body 1102 dilates in direction 1112, such that stent body 1102 stays in contact and follows peristaltic wave 1110. Optionally, stent body 1102 may be disposed with grip regions 1106 with peristaltic wave periodicity as illustrated in FIG. 9.

Figure 12:
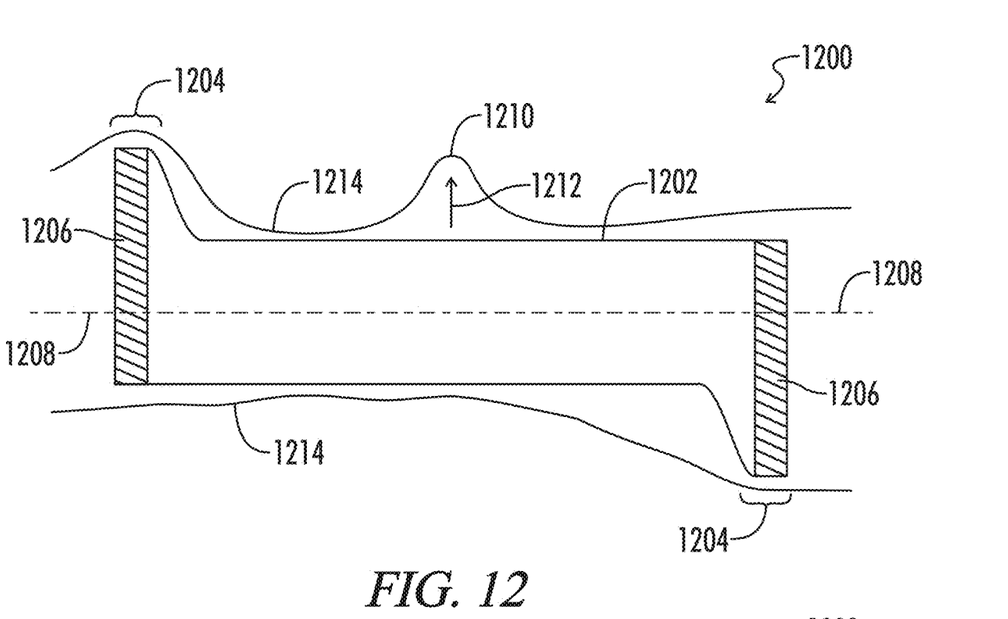
FIG. 12 depicts a stent comprising dilated or flared regions that are displaced with respect to the stent body centerline.

With reference to FIG. 12, an esophageal stent 1200 comprises a stent body 1202 and dilated regions 1204 where surface texture 1206 is disposed over the stent body 1202. Cuff or flare regions 1204 are displaced with respect to stent body centerline 1208. The displacements of the two cuff or flare regions 1204 are ideally 180 degrees out of phase, such that one end is displaced "up" and the other end is displaced "down". This configuration induces the middle part of stent body 1202 to deflect in direction 1212 with respect to peristaltic wave 1210. Accordingly, stent body 1202 follows peristaltic wave 1210.

Figure 13:
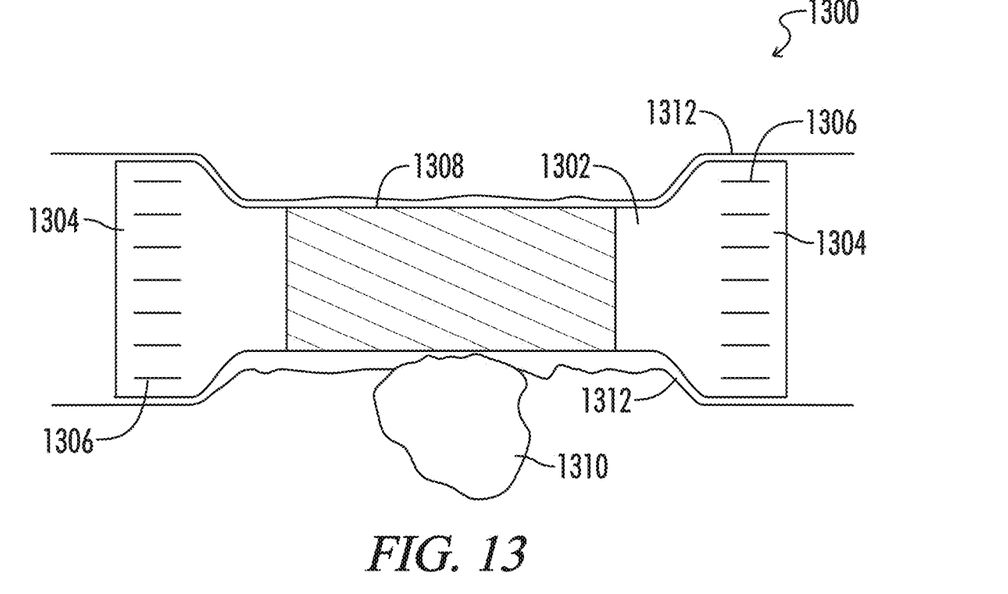
FIG. 13 depicts a stent comprising slip ribs and a surface texture region. The surface texture region in this embodiment is capable of engaging with an esophageal growth in the esophagus.

With reference to FIG. 13, an esophageal stent 1300 comprises a stent body 1302 and cuff or flare regions 1304 where slip ribs 1306 are disposed over the stent body 1302. The primary fixation region 1308 is designed to engage an esophageal growth 1310 on esophagus 1312. Optionally, region 1308 may be radially reinforced, or stiffer than dilated regions 1304. Optionally one cuff or flare region 1304 may be gripping, rather than slipping.

Alternatively, some of the wires through which the strips are woven can be separate from the stent construction, such that when they are removed, the interwoven pattern is undone, and the textured strips are released from the stent.

The description provided herein is not to be limited in scope by the specific embodiments described which are intended as single illustrations of individual aspects of certain embodiments. The methods, compositions and devices described herein can comprise any feature described herein either alone or in combination with any other feature (s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference in their entirety into the specification to the same extent as if each individual publication, patent or patent application was specifically and individually indicated to be incorporated herein by reference. Citation or discussion of a reference herein shall not be construed as an admission that such is prior art.

Thus, although there have been described particular embodiments of the present invention of a new and useful Stents with Improved Fixation it is not intended that such references be construed as limitations upon the scope of this invention except as set forth in the following claims.

What is claimed is:

1. A device for fixation in a body lumen, comprising:
   a tubular stent of open weave construction having a stent body having an axial length, the stent body comprising a first, a second end, and a medial region, the stent having a first configuration and a second configuration, the second configuration being radially compressed to a reduced radius when compared to the first configuration; and
   a continuous elastomeric film disposed axially along the stent, the continuous film circumscribing the stent over substantially the entirety of the axial length to define a barrier region; and
   wherein a portion of the barrier region comprises a surface texture, the surface texture providing a fixation region of the stent for fixing the stent within the body lumen, and
   wherein the surface texture comprises hierarchical microstructures, the hierarchical microstructures including a plurality of first microfeatures and a plurality of second microfeatures, the plurality of first microfeatures configured to develop a hydrophobic region and the plurality of second microfeatures configured to develop a hydrophilic region, wherein at least one dimension of a first microfeature of the plurality of first microfeatures and at least one dimension of a second microfeature of the plurality of second microfeatures has a ratio of dimensions greater than 2.

2. The device of claim 1 wherein:
the tubular stent is flexible and assumes the second configuration in response to application of an external force, and assumes the first configuration in the absence of the external force.

3. The device of claim 2 wherein the elastomeric film reinforces the tubular stent along the barrier region.

4. The device of claim 3 wherein the elastomeric film comprises silicone.

5. The device of claim 3, wherein, upon removal of the external force, the fixation region of the tubular stent exerts a lower restoring force in its return toward the first configuration relative to a non-textured region of the tubular stent.

6. The device of claim 5, wherein the fixation region comprises at least one inflatable annulus.

7. The device of claim 5, wherein the fixation region comprises at least one elastic polymeric torus.

8. The device of claim 1, wherein the first end comprises a first cuff and the second end comprises a second cuff, the first and second cuffs each having a surface texture disposed thereon.

9. The device of claim 8 wherein each of the surface textures is provided in a segmented pattern on the first and second cuffs.

10. The device of claim 1, wherein the barrier region has a diameter less than the diameter of the fixation region when the stent is in the first configuration.

11. The device of claim 1, further comprising a removable delivery sleeve having a low durometer, the delivery sleeve disposed on an outer surface of the tubular stent, wherein the delivery sleeve separates the body lumen from the fixation region of the tubular stent to allow positioning of the tubular stent within the body lumen without engaging the fixation region with the body lumen.

12. The device of claim 1, wherein a circumferential ring of anchoring elements is positioned in the medial region of the tubular stent.

13. The device of claim 1, wherein the tubular stent further comprises the first end or second end having a flared region comprising the surface texture, and a lubricious region disposed on the medial region.

14. The device of claim 1, wherein at least the first end or the second end is lubricious.

* * * * *